United States Patent
Galli et al.

(10) Patent No.: US 7,456,171 B2
(45) Date of Patent: Nov. 25, 2008

(54) 1,4-DIAZABICYCLO[3.2.2]NONANE-CARBOXAMIDE DERIVATIVES, PREPARATION AND THERAPEUTIC USE THEREOF

(75) Inventors: Frederic Galli, Vaucresson (FR); Patrick Lardenois, Bourg-la-Reine (FR); Odile Leclerc, Massy (FR); Alistair Lochead, Charenton le Pont (FR)

(73) Assignee: Sanofi-Aventis, Paris (FR)

( * ) Notice: Subject to any disclaimer, the term of this patent is extended or adjusted under 35 U.S.C. 154(b) by 292 days.

(21) Appl. No.: 11/098,670

(22) Filed: Apr. 4, 2005

(65) Prior Publication Data

US 2005/0182062 A1    Aug. 18, 2005

Related U.S. Application Data

(63) Continuation of application No. PCT/FR03/002929, filed on Oct. 6, 2003.

(30) Foreign Application Priority Data

Oct. 8, 2002    (FR) .................... 02 12500

(51) Int. Cl.
| | |
|---|---|
| *A61P 25/00* | (2006.01) |
| *A61K 31/55* | (2006.01) |
| *A61K 31/551* | (2006.01) |
| *C07D 487/08* | (2006.01) |
| *C07D 519/00* | (2006.01) |

(52) U.S. Cl. ...................... 514/221; 540/556
(58) Field of Classification Search ............ 514/221; 540/556
See application file for complete search history.

(56) References Cited

U.S. PATENT DOCUMENTS

2006/0052368 A1*   3/2006   Ernst et al. .............. 514/221

FOREIGN PATENT DOCUMENTS

| EP | 0 307 140 A1 | 3/1989 |
|---|---|---|
| EP | 1 219 622 A2 | 7/2002 |
| EP | 1 219 622 A3 | 7/2002 |
| WO | WO 00/34279 | 6/2000 |
| WO | WO 01/55150 A1 | 8/2001 |
| WO | WO 01/92261 A1 | 12/2001 |

* cited by examiner

*Primary Examiner*—Brenda L Coleman
(74) *Attorney, Agent, or Firm*—Balaram Gupta

(57) ABSTRACT

The present invention discloses and claims compounds of general formula

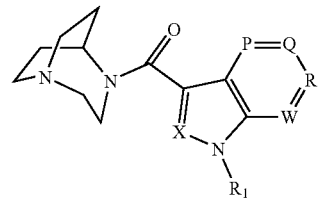

in which X represents a nitrogen atom or a group of formula C—$R_2$, P represents a group of formula C—$R_3$, Q represents a group of formula C—$R_4$, R represents a group of formula C—$R_5$, W represents a group of formula C—$R_6$, or one of the symbols P, Q, R and W represents a nitrogen atom, $R_1$ represents a hydrogen atom or an alkyl group, $R_2$ represents a hydrogen atom or an alkyl group, $R_3$, $R_4$, $R_5$ and $R_6$ each represent a hydrogen or halogen atom, or an alkyl, alkoxy, nitro, amino, trifluoromethyl, cyano or amino group or other functional groups. The compounds of the invention are useful in a variety of therapeutic applications.

16 Claims, No Drawings

1,4-DIAZABICYCLO[3.2.2]NONANE-CARBOXAMIDE DERIVATIVES, PREPARATION AND THERAPEUTIC USE THEREOF

This application is a continuation of International application No. PCT/FR2003/002,929, filed Oct. 6, 2003, which is incorporated herein by reference in its entirety; which claims the benefit of priority of French Patent Application No. 02/12,500, filed Oct. 8, 2002.

BACKGROUND OF THE INVENTION

Field of the Invention

The compounds of the present invention are nicotinic ligands. These compounds are useful in the treatment or prevention of disorders associated with dysfunction of the nicotinic receptors, especially in the central nervous system.

SUMMARY OF THE INVENTION

The compounds of the invention correspond to the general formula (I)

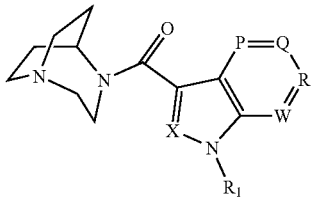

(I)

in which

X represents a nitrogen atom or a group of general formula C—$R_2$,

P represents a group of general formula C—$R_3$,
Q represents a group of general formula C—$R_4$,
R represents a group of general formula C—$R_5$,
W represents a group of general formula C—$R_6$,
or one of the symbols P, Q, R and W represents a nitrogen atom,
$R_1$ represents a hydrogen atom or a ($C_1$-$C_6$)alkyl group,
$R_2$ represents a hydrogen atom or a ($C_1$-$C_6$)alkyl group,
$R_3$, $R_4$, $R_5$ and $R_6$ each represent, independently of each other, a hydrogen or halogen atom, or a ($C_1$-$C_6$)alkyl, ($C_1$-$C_6$) alkoxy, nitro, amino, trifluoromethyl or cyano group, or a group of general formula —$NR_7R_8$, —$NR_7C(\!=\!O)R_8$, —$NR_7C(\!=\!O)NR_8R_9$, —$NR_7C(\!=\!O)OR_8$, —$NR_7S(\!=\!O)_2NR_8R_9$, —$OR_7$, —$OC(\!=\!O)R_7$, $OC(\!=\!O)OR_7$, —$OC(\!=\!O)ONR_7R_8$, —$OC(\!=\!O)SR_7$, —$OS(\!=\!O)_2R_7$, —$C(\!=\!O)OR_7$, —$C(\!=\!O)R_7$, —$C(\!=\!O)NR_7R_8$, —$SR_7$, —$S(\!=\!O)R_7$, —$S(\!=\!O)_2R_7$, —$S(\!=\!O)_2NR_7R_8$, ($C_6$-$C_{11}$) aryl or ($C_3$-$C_{12}$)heteroaryl, optionally substituted with one or more groups chosen from halogen atoms and ($C_1$-$C_6$) alkyl, ($C_1$-$C_6$)alkoxy, nitro, amino, trifluoromethyl and cyano groups, or groups of general formula —$NR_7R_8$ or —$OR_7$,
$R_7$, $R_8$ and $R_9$ each represent, independently of each other, a hydrogen atom or a linear or branched ($C_1$-$C_6$)alkyl group, a linear or branched ($C_2$-$C_6$)alkenyl group, a linear or branched ($C_2$-$C_6$)alkynyl group, a ($C_3$-$C_8$)cycloalkyl or ($C_4$-$C_8$)cycloalkenyl group, or a heterocycloalkyl group containing 3 to 8 atoms in the ring, or a ($C_5$-$C_{11}$)bicycloalkyl or ($C_7$-$C_{11}$)bicycloalkenyl group, a heterobicycloalkyl group containing 5 to 11 atoms in the ring, a bicycloheteroalkenyl group containing 5 to 11 atoms in the ring, or a ($C_6$-$C_{11}$)aryl or heteroaryl group containing 5 to 12 atoms in the ring, $R_7$, $R_8$ and $R_9$ may be optionally substituted, independently of each other, with a halogen atom or a ($C_1$-$C_6$)alkyl, ($C_1$-$C_6$) alkoxy, nitro, amino, trifluoromethyl or cyano group, or a group of general formula —$NR_{10}R_{11}$, —$NR_{10}C(\!=\!O)R_{11}$, —$NR_{10}C(\!=\!O)NR_{11}R_{12}$, —$NR_{10}C(\!=\!O)OR_{11}$, —$NR_{10}S(\!=\!O)_2NR_{11}R_{12}$, —$OR_{10}$, —$OC(\!=\!O)R_{10}$, —$OC(\!=\!O)OR_{10}$, —$OC(\!=\!O)ONR_{10}R_{11}$, —$OC(\!=\!O)SR_{10}$, —$C(\!=\!O)OR_{10}$, —$C(\!=\!O)R_{10}$, —$C(\!=\!O)NR_{10}R_{11}$, —$SR_{10}$, —$S(\!=\!O)R_{10}$, —$S(\!=\!O)_2R_{10}$, —$S(\!=\!O)_2NR_2R_{11}$, $R_{10}$, $R_{11}$ and $R_{12}$ each represent, independently of each other, a hydrogen atom or a linear or branched ($C_1$-$C_6$)alkyl group, a linear or branched ($C_2$-$C_6$)alkenyl group, a linear or branched ($C_2$-$C_6$)alkynyl group, a ($C_3$-$C_8$)cycloalkyl or ($C_4$-$C_8$)cycloalkenyl group, a heterocycloalkyl group containing 3 to 8 atoms in the ring, a ($C_5$-$C_{11}$)bicycloalkyl or ($C_7$-$C_{11}$)bicycloalkenyl group, a heterobicycloalkyl group containing 5 to 11 atoms in the ring, a bicycloheteroalkenyl group containing 5 to 11 atoms in the ring, or a ($C_6$-$C_{11}$) aryl or heteroaryl group containing 5 to 12 atoms in the ring, $R_{10}$, $R_{11}$ and $R_{12}$ may be optionally substituted, independently of each other, with a halogen atom or a ($C_1$-$C_6$)alkyl, ($C_1$-$C_6$)alkoxy, nitro, amino, trifluoromethyl or cyano group, or —$NR_{13}R_{14}$, —$NR_{13}C(\!=\!O)R_{14}$, —$NR_{13}C(\!=\!O)NR_{14}R_{15}$, —$NR_{13}C(\!=\!O)OR_{14}$, —$NR_{13}S(\!=\!O)_2NR_{14}R_{15}$, —$OR_{13}$, —$OC(\!=\!O)R_{13}$, —$OC(\!=\!O)OR_{13}$, —$OC(\!=\!O)ONR_{13}R_{14}$, —$OC(\!=\!O)SR_{13}$, —$C(\!=\!O)OR_{13}$, —$C(\!=\!O)R_{13}$, —$C(\!=\!O)NR_{13}R_{14}$, —$SR_{13}$, —$S(\!=\!O)R_{13}$, —$S(\!=\!O)_2R_{13}$, —$S(\!=\!O)_2NR_{13}R_{14}$, $R_{13}$, $R_{14}$ and $R_{15}$ each represent, independently of each other, a hydrogen atom or a linear or branched ($C_1$-$C_6$)alkyl group, a linear or branched ($C_2$-$C_6$)alkenyl group, a linear or branched ($C_2$-$C_6$)alkynyl group, a ($C_3$-$C_8$)cycloalkyl or ($C_4$-$C_8$)cycloalkenyl group, a heterocycloalkyl group containing 3 to 8 atoms in the ring, a ($C_5$-$C_{11}$)bicycloalkyl or ($C_7$-$C_{11}$)bicycloalkenyl group, a heterobicycloalkyl group containing 5 to 11 atoms in the ring, a bicycloheteroalkenyl group containing 5 to 11 atoms in the ring or a ($C_6$-$C_{11}$)aryl or heteroaryl group containing 5 to 12 atoms in the ring, and $R_3$ and $R_4$, or $R_4$ and $R_5$, or $R_5$ and $R_6$, may together form, with the two carbon atoms that bear them, another aromatic or heteroaromatic ring containing 6 atoms in the ring, optionally substituted with 1 to 4 substituents chosen from those defined for $R_7$, $R_8$ and $R_9$.

DETAILED DESCRIPTION OF THE INVENTION

A first subset of advantageous compounds is that of the compounds of general formula (I) in which X represents a group of general formula C—$R_2$ as defined above.

Among these compounds that may be distinguished, on the one hand, are the compounds of general formula (I) in which P, Q, R and W each represent, respectively, a group of general formula C—$R_3$, C—$R_4$, C—$R_5$ and C—$R_6$, as defined above, and, on the other hand, the compounds of general formula (I) in which one of the symbols P, Q, R and W represents a nitrogen atom.

A second subset of advantageous compounds is that of the compounds of general formula (I) in which X represents a nitrogen atom.

Among these compounds that may be distinguished, on the one hand, are the compounds of general formula (I) in which P, Q, R and W each represent, respectively, a group of general formula C—R₃, C—R₄, C—R₅ and C—R₆, as defined above, and, on the other hand, the compounds of general formula (I), in which one of the symbols P, Q, R and W represents a nitrogen atom.

The compounds of the invention may exist in the form of bases or of addition salts with acids.

In accordance with the invention, the compounds of general formula (I) may be prepared via a process illustrated by Scheme 1 below.

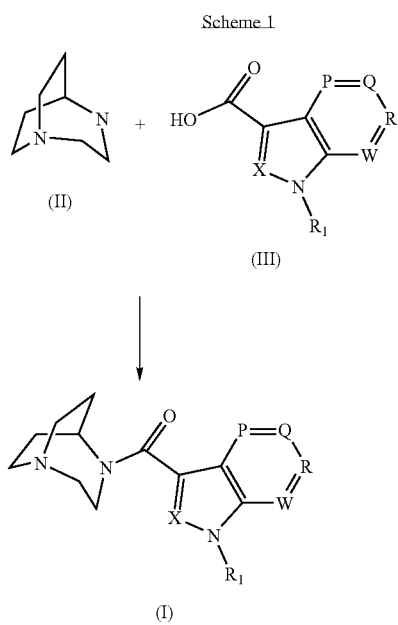

1,4-Diazabicyclo[3.2.2]nonane of general formula (II) is reacted with a compound of general formula (III), in which X, P, Q, R, W and $R_1$ are as defined above, in the presence of a coupling agent such as, for example, N,N'-carbonyldiimidazole, in a solvent such as N,N-dimethylformamide. Alternatively, the carboxylic acid function present on the compound of general formula (III) may be converted, in a prior step, to an acid chloride function to react with the 1,4-diazabicyclo[3.2.2]nonane in a solvent such as dichloroethane.

The compounds of general formula (I) may also be prepared via a process illustrated by Scheme 2 below.

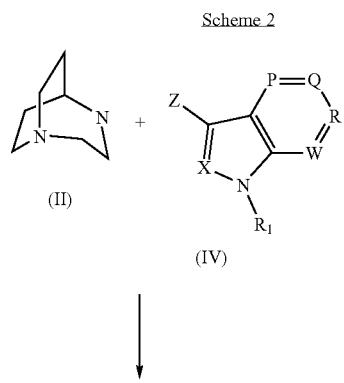

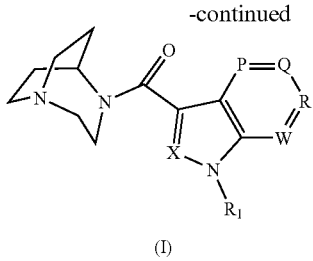

1,4-Diazabicyclo[3.2.2]nonane of general formula (II) is reacted with a compound of general formula (IV) in which X, P, Q, R, W and $R_1$ are as defined above, and Z represents a bromine or iodine atom, in the presence of carbon monoxide and a palladium catalyst such as, for example, bis(triphenylphosphino)dichloropalladium, and a base such as, for example, triethylamine, in a solvent such as, for example, N,N-dimethylformamide.

For certain compounds, the substituents may not be present in the starting compound of general formula (III) or in (IV); depending on their nature, these substituents may be introduced onto the final compound of general formula (I). Thus, for example, compounds of general formula (I) in which P, Q, R and W each represent, respectively, a group of general formula C—R₃, C—R₄, C—R₅ and C—R₆ in which R₃, R₄, R₅ and R₆ each represent a $(C_6-C_{11})$aryl or $(C_5-C_{12})$heteroaryl group, may be prepared from the corresponding compounds, in which formula R₃, R₄, R₅ and R₆ each represent a bromine or iodine atom, according to any known method, such as a coupling of Suzuki type in the presence of a boronic acid and a palladium catalyst, for example tetrakis(triphenylphosphine)palladium.

The compounds of general formula (III) are commercially available or are available via methods described in the literature, for instance in *Can. J. Chem.* 1988, 66, 420-8.

The compounds of general formula (IV) are commercially available or are available via methods described in the literature, for instance in *J. Het. Chem.* 1983, 475.

The preparation of 1,4-diazabicyclo[3.2.2]-nonane is described in *J. Med. Chem.* 1993, 36, 2311-2320.

The examples that follow illustrate the preparation of a number of compounds of the invention. The elemental microanalyses and the IR and NMR spectra confirm the structures of the compounds obtained.

The numbers indicated in parentheses in the example titles correspond to those in the first column of the table given later.

In the compound names, the hyphen "-" forms a part of the word, and the underscore mark "_" serves merely to indicate the line break; it should be deleted if it does not occur at a line break, and should not be replaced either with a normal hyphen or with a space.

EXAMPLE 1 (COMPOUND 2)

3-(1,4-Diazabicyclo[3.2.2]non-4-ylcarbonyl)-1H-indazole hydrochloride 2.4 g (14.8 mmol) of 1H-indazole-3-carboxylic acid dissolved in 30 ml of N,N-dimethylformamide and 2.4 g (14.8 mmol) of N,N'-carbonyldiimidazole are introduced into a 100 ml reactor. The mixture is stirred at room temperature for 45 minutes, 1.7 g (13.4 mmol) of 1,4-diazabicyclo[3.2.2]nonane dissolved in 20 ml of N,N-dimethylformamide are then added and the mixture is stirred at room temperature for 15 hours.

The resulting mixture is diluted in 100 ml of ethyl acetate and the organic phase is washed with 100 ml of saturated aqueous sodium chloride solution, dried and filtered. The solvent is concentrated under reduced pressure and the residue is purified by chromatography on a column of silica gel, eluting with a mixture of chloroform, methanol and aqueous ammonia in 85/15/1.5 proportions. 1.7 g of product are obtained, and are dissolved in 30 ml of isopropyl alcohol, followed by addition of 1.5 ml of a 5N solution of hydrogen chloride in isopropyl alcohol. The crystals obtained are collected by filtration and dried under reduced pressure.

1.2 g of hydrochloride are obtained.
Melting point: 282-283° C.

EXAMPLE 2 (COMPOUND 8)

3-(1,4,Diazabicyclo[3.2.2]non-4-ylcarbonyl)-1H-pyrazolo[3,4-c]pyridine 1 g (5 mmol) of 3-bromo-1H-pyrazolo[3,4-c]pyridine, 0.53 g (0.75 mmol) of bis(triphenyl-phosphino)dichloropalladium, 1.9 g (15.1 mmol) of 1,4-diazabicyclo[3.2.2]nonane and 3.5 ml (25 mmol) of triethylamine dissolved in 15 ml of N,N-dimethyl-formamide are successively introduced into a 50 ml reactor. The mixture is then purged with carbon monoxide and heated at 110° C. for 20 hours. The reaction medium is poured into 100 ml of water and the aqueous phase is extracted with chloroform. After drying the organic phases, they are dried, filtered and concentrated under reduced pressure. The residue is purified by chromatography on a column of silica gel, eluting with a mixture of chloroform, methanol and aqueous ammonia in 90/10/1 proportions.

0.41 g of product in the form of a crystalline solid is thus obtained.
Melting point: 232-234° C.

EXAMPLE 3 (COMPOUND 1)

4-(1H-Indol-3-ylcarbonyl)-1,4-diazabicyclo[3.2.2]nonane hydrochloride

By analogy with Example 1, 0.117 g (0.72 mmol) of 1H-indole-3-carboxylic acid is reacted with 0.083 g (0.66 mmol) of 1,4-diazabicyclo[3.2.2]-nonane under the conditions described in Example 1.

0.008 g of hydrochloride is obtained.
Melting point: 332-333° C.

EXAMPLE 4 (COMPOUND 6)

3-(1,4-Diazabicyclo[3.2.2]non-4-ylcarbonyl)-1H-pyrrolo[2,3-b]pyridine hydrochloride By analogy with Example 2, 0.5 g (2.05 mmol) of 3-iodo-1H-pyrrolo[2,3-b]pyridine with 0.52 g (4.1 mmol) of 1,4-diazabicyclo[3.2.2]nonane under the conditions described in Example 2.

0.13 g of hydrochloride are obtained.
Melting point: >300° C.

EXAMPLE 5 (COMPOUND 9)

3-(Diazabicyclo[3.2.2]non-4-ylcarbonyl)-6-methyl-1H-pyrazolo[3,4-b]pyridine hydrobromide By analogy with Example 2, 0.105 g (0.5 mmol) of 3-bromo-6-methyl-1H-pyrazolo[3,4-b]pyridine with 0.108 g (0.86 mmol) of 1,4-diazabicyclo[3.2.2]nonane under the conditions described in Example 2.

0.16 g of hydrobromide is obtained.
Melting point: >300° C.

EXAMPLE 6 (COMPOUND 27)

3-(1,4-Diazabicyclo[3.2.2]non-4-ylcarbonyl)-6-(5-methyl-2-thienyl)-1H-indazole bromohydride 0.1 g (0.29 mmol) of 5-bromo-3-(1,4-diaza-bicyclo[3.2.2]non-4-ylcarbonyl)-1H-indazole, 0.057 g (0.4 mmol) of 5-methyl-2-thiopheneboronic acid, 0.016 g (0.01 mol) of tetrakis(triphenylphosphino)-palladium, 0.058 G (0.27 mmol) of sodium carbonate, 2 ml of toluene and 0.2 ml of ethanol are successively introduced into a 10 ml reactor and the mixture is heated at 100° C. for 4 hours. The resulting mixture is hydrolyzed with 2 ml of water, the aqueous phase is extracted with chloroform and the combined organic phases are dried over magnesium sulfate, filtered and concentrated under reduced pressure. The residue is purified by chromatography on a silica plate, eluting with a 90/10/1 mixture of chloroform, methanol and aqueous ammonia.

0.083 g of product is obtained, which is dissolved in 2 ml of isopropyl alcohol, followed by addition of 0.08 ml of a 5.7N solution of hydrogen bromide in acetic acid. The crystals formed are collected by filtration and dried under vacuum.

0.068 g of product is obtained.
Melting point: 339-340° C.

EXAMPLE 7 (COMPOUND 83)

3-(1,4-Diazabicyclo[3.2.2]non-4-ylcarbonyl)-6-(4-fluorophenyl)-1H-pyrrolo[2,3-b]pyridine 7.1. 2,2,2-Trichloro-1-(6-chloro-1H-pyrrolo[2,3-b]pyrid-3-yl)ethanone 4 g (0.03 mol) of aluminum trichloride, 3 ml of dichloromethane and 3.6 g (0.02 mol), i.e. 2.23 ml, of trichloroacetyl chloride are placed in a round-bottomed flask with a condenser, a magnetic stirrer and a calcium chloride guard tube, and the mixture is stirred at room temperature for 30 minutes.

1.52 g (0.01 mol) of 6-chloro-1H-pyrrolo[2,3-b]pyridine are added portionwise and the mixture is refluxed for 3 hours.

While cooling in an ice bath, 50 ml of ice are added to the flask and the mixture is stirred vigorously for 30 minutes.

A pasty mass is obtained, which is separated from the aqueous phase by decantation.

The product is used directly in the next step.

7.2. 6-Chloro-1H-pyrrolo[2,3-b]pyridine-3-carboxylic acid

The crude derivative from the preceding step is taken up in 10 ml of water and 6 ml of 35% sodium hydroxide, and the mixture is heated in an oil bath at 90° C. for 10 minutes. After cooling, the reaction medium is filtered, the filtrate is cooled in an ice bath and is acidified to about pH 3 with concentrated hydrochloric acid. A white precipitate is obtained, which is filtered, drained by suction and dried in a desiccator under vacuum.

1.72 g of product are isolated.
Melting point: 283-284° C.

7.3. 6-Chloro-3-(1,4-diazabicyclo[3.2.2]non-4-ylcarbonyl)-1H-pyrrolo[2,3-b]pyridine
(Compound No. 82)

375 mg (2 mmol) of the derivative from the preceding step, 760 mg (4 mmol) of 1-(3-dimethylaminopropyl)-3-ethylcarbodiimide hydrochloride, 50 mg of dimethylaminopyridine, 5 ml of acetonitrile and 500 mg (4 mmol) of diazabicyclononane are placed in a microwave tube (Personal Chemistry), and the tube is stoppered and heated at 100° C. for 10 minutes. The mixture is immersed in 50 ml of water and extracted with dichloromethane, and the organic phase is evaporated. By trituration in isopropyl ether, 310 mg of a crystalline compound are obtained.

Melting point: 228-229° C.

7.4. 3-(1,4-Diazabicyclo[3.2.2]non-4-ylcarbonyl)-6-(4-fluorophenyl)-1H-pyrrolo[2,3-b]pyridine 87 mg (0.287 mmol) of the derivative obtained in the preceding step, 80 mg (2 equivalents) of (4-fluorophenyl)boronic acid, 20 mg of tetrakis(triphenylphosphine)palladium (0), 2 ml of toluene, 2 ml of acetonitrile and 2 ml of 2N sodium carbonate solution are placed in a microwave tube (Personal Chemistry) and the mixture is heated at 150° C. for 10 minutes.

The organic phase is deposited on a silica cartridge and eluted with a 90/10/1 mixture of dichloromethane, methanol and aqueous ammonia.

The oily residue obtained crystallizes by trituration in isopropyl ether.

60 mg of this product are isolated.

Melting point: 285-286° C.

The table that follows illustrates the chemical structures and the physical properties of a number of compounds of the invention.

In the P, Q, R and W columns, "Ms" denotes a methylsulfonyl group, $iC_3H_7$ denotes a 1-methylethyl group, $x\text{-}C_4H_3S$ denotes an x-thienyl group, $x\text{-}C_4H_3O$ denotes an x-furyl group, $x\text{-}C_4H_4N$ denotes an x-pyrrolyl group and $x\text{-}C_5H_4N$ denotes an x-pyridyl group.

In the "salt" column, "-" denotes a compound in base form, "HBr" denotes a hydrobromide and "HCl" denotes a hydrochloride and "ox." Denotes an oxalate.

TABLE (I)

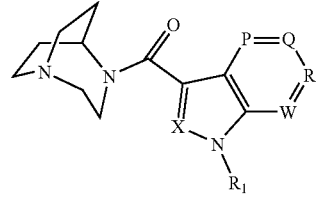

| No. | X | $R_1$ | P | Q | R | W | Salt | m.p. (° C.) |
|---|---|---|---|---|---|---|---|---|
| 1 | CH | H | CH | CH | CH | CH | HCl | 332-333 |
| 2 | N | H | CH | CH | CH | CH | HCl | 282-283 |
| 3 | CH | $CH_3$ | CH | CH | CH | CH | HCl | 227-228 |
| 4 | N | H | CH | CH | C—$CH_3$ | CH | HCl | 339-340 |
| 5 | N | H | CH | CH | C—$NO_2$ | CH | — | 209-210 |
| 6 | CH | H | CH | CH | CH | N | HCl | >300 |
| 7 | N | H | CH | CH | CH | N | HCl | >325 |
| 8 | N | H | CH | CH | N | CH | — | 232-234 |
| 9 | N | H | CH | CH | C—$CH_3$ | N | HBr | >300 |
| 10 | N | H | CH | C—F | CH | CH | HBr | 337-338 |
| 11 | N | H | CH | CH | C—Cl | CH | HBr | 336-337 |
| 12 | N | H | CH | C—Br | CH | CH | HBr | 364-365 |
| 13 | N | H | Ch | C—OMs | CH | CH | ox. | 242-243 |
| 14 | Ch | H | Ch | C—$C_6H_5$ | CH | CH | HCl | 322.6 |
| 15 | Ch | H | Ch | C-(4-F—$C_6H_4$) | CH | CH | HCl | 356.5 |
| 16 | CH | H | CH | C-(4-Cl—$C_6H_4$) | CH | CH | HCl | 316 |
| 17 | CH | H | CH | C-(4-$CH_3$—$C_6H_4$) | CH | CH | HCl | 289.2 |
| 18 | CH | H | CH | C-(4-$(CH_2)_4$—$C_6H_4$) | CH | CH | HCl | 350.2 |
| 19 | CH | H | CH | C-(4-$CF_3$—$C_6H_4$) | CH | CH | HCl | 293.8 |
| 20 | CH | H | CH | C-(4-$OCH_3$—$C_6H_4$) | CH | CH | HCl | 300.9 |
| 21 | CH | H | CH | C-(4-$OCF_3$—$C_6H_4$) | CH | CH | HCl | 292 |
| 22 | CH | H | CH | C-(3-Cl-4-F—$C_6H_3$) | CH | CH | HCl | 321.6 |
| 23 | CH | H | CH | C-(3,4-$Cl_2$—$C_6H_3$) | CH | CH | HCl | |
| 24 | CH | H | CH | C-(2,3-$Cl_2$—$C_6H_3$) | CH | CH | HCl | 260.9 |
| 25 | CH | H | CH | C-(3-F-4-$OCH_3$—$C_6H_5$) | CH | CH | HCl | 287.1 |
| 26 | N | H | CH | C—$CH_3$ | CH | CH | HBr | 291-292 |
| 27 | N | H | CH | C-(5-$CH_3$-2-$C_4H_3S$) | CH | CH | HBr | 339-340 |
| 28 | N | H | CH | C—Cl | CH | CH | — | 248-249 |
| 29 | CH | H | CH | C-(3-F—$C_6H_4$) | CH | CH | HCl | 250-252 |
| 30 | CH | H | CH | C-(3-CN—$C_6H_4$) | CH | CH | HCl | 221-223 |
| 31 | CH | H | CH | C-(3-$CH_3$—$C_6H_4$) | CH | CH | HCl | 367-369 |
| 32 | CH | H | CH | C-(3-$(CH(CH_3)_2$—$C_6H_4$) | CH | CH | HCl | 174-176 |
| 33 | CH | H | CH | C-(3-$CF_3$—$C_6H_4$) | CH | CH | ox. | 258-260 |
| 34 | CH | H | CH | C-(3-$OCH_3$—$C_6H_4$) | CH | CH | HCl | 199-201 |
| 35 | CH | H | CH | C-(3-$OCH_2CH_2CH_3$—$C_6H_4$) | CH | CH | HCl | 263-265 |
| 36 | CH | H | CH | C-3-$C_4H_3S$ | CH | CH | HCl | 279-281 |
| 37 | CH | H | CH | C-2-$C_4H_3S$ | CH | CH | HCl | 231-233 |

TABLE-continued

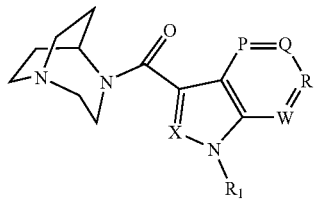
(I)

| No. | X | $R_1$ | P | Q | R | W | Salt | m.p. (° C.) |
|---|---|---|---|---|---|---|---|---|
| 38 | CH | H | CH | C-(5-$CH_3$-2-$C_4H_3S$) | CH | CH | HCl | 280-282 |
| 39 | CH | H | CH | C-(4-$CH_3$-2-$C_4H_3S$) | CH | CH | HCl | 369-371 |
| 40 | CH | H | CH | C-2-$C_4H_3O$ | CH | CH | HCl | 258-260 |
| 41 | CH | H | CH | C-3-$C_4H_3O$ | CH | CH | HCl | 313-315 |
| 42 | N | H | CH | C—$OCH_3$ | CH | CH | — | 212-213 |
| 43 | N | H | CH | CH | C—$CF_3$ | CH | HBr | 290-292 |
| 44 | N | H | CH | CH | C—Br | CH | — | 195-196 |
| 45 | N | H | CH | CH | C-2-$C_4H_3S$ | CH | — | 263-264 |
| 46 | N | H | CH | C-2-$C_4H_3S$ | CH | CH | HBr | 329-330 |
| 47 | N | H | N | CH | CH | CH | HBr | 312-315 |
| 48 | N | H | CH | CH | C-2-$C_4H_3O$ | CH | — | 242-243 |
| 49 | N | H | CH | CH | C—$NH_2$ | CH | ox. | 295-296 |
| 50 | N | H | CH | C-2-$C_4H_3O$ | CH | CH | HBr | 321-322 |
| 51 | CH | H | CH | CH | CH | C—$C_6H_5$ | HCl | 222-224 |
| 52 | CH | H | CH | CH | CH | C-(4-F-$C_6H_4$) | HCl | 264-266 |
| 53 | CH | H | CH | CH | CH | C-(4-Cl—$C_6H_4$) | HCl | 369-371 |
| 54 | CH | H | CH | CH | CH | C-(4-$CH_3$—$C_6H_4$) | HCl | 303-305 |
| 55 | CH | H | CH | CH | CH | C-(4-$C_4H_9$—$C_6H_4$) | HCl | 254-256 |
| 56 | CH | H | CH | CH | CH | C-(4-$CF_3$—$C_6H_4$) | HCl | 226-228 |
| 57 | CH | H | CH | CH | CH | C-(4-$OCH_3$—$C_6H_4$) | HCl | 306-308 |
| 58 | CH | H | CH | CH | CH | C-(4-$OCF_3$—$C_6H_4$) | HCl | 305-307 |
| 59 | CH | H | CH | CH | CH | C-(3-F—$C_6H_4$) | HCl | 286-288 |
| 60 | CH | H | CH | CH | CH | C-(3-CN—$C_6H_4$) | HCl | 189-191 |
| 61 | CH | H | CH | CH | CH | C-(3-$CH_3$—$C_6H_4$) | HCl | 261-263 |
| 62 | CH | H | CH | CH | CH | C-(4-$iC_3H_7$—$C_6H_4$) | HCl | 293-295 |
| 63 | CH | H | CH | CH | CH | C-(3-$OCF_3$—$C_6H_4$) | HCl | 302-304 |
| 64 | CH | H | CH | CH | CH | C-3-$C_4H_3S$ | HCl | 317-319 |
| 65 | CH | H | CH | CH | CH | C-(5-$CH_3$-2-$C_4H_3S$) | HCl | |
| 66 | CH | H | CH | CH | CH | C-3-$C_4H_3O$ | HCl | |
| 67 | CH | H | CH | CH | CH | C-4-$C_5H_4N$ | HCl | |
| 68 | CH | H | CH | CH | CH | C—Br | — | 197-199 |
| 69 | CH | H | CH | CH | CH | C-3-$C_5H_4N$ | HCl | |
| 70 | N | H | CH | C-2-$C_4H_4N$ | CH | CH | ox. | 171-172 |
| 71 | CH | H | CH | C—Br | CH | CH | — | 237-239 |
| 72 | CH | H | CH | CH | C—Br | CH | — | 237-239 |
| 73 | N | H | C—Cl | CH | CH | CH | HCl | 339-340 |
| 74 | N | H | CH | CH | CH | C—$CH_3$ | HCl | 327-328 |
| 75 | N | H | CH | CH | CH | C—Cl | HCl | 316-317 |
| 76 | N | H | CH | N | CH | CH | — | 217-219 |
| 77 | N | H | CH | CH | CH | C—$OCH_3$ | — | 272-273 |
| 78 | N | H | CH | C—$CH_3$ | CH | C—Cl | HCl | 313-314 |
| 79 | N | H | C—F | OH | CH | CH | HBr | 302-303 |
| 80 | N | H | CH | C—Br | CH | C—$CH_3$ | HBr | 305-306 |
| 81 | N | H | CH | CH | C-3-$C_4H_3O$ | CH | HBr | 331-332 |
| 82 | CH | H | CH | CH | C—Cl | N | — | 228-229 |
| 83 | CH | H | CH | CH | C-(4-F—$C_6H_4$) | N | — | 285-286 |
| 84 | N | H | CH | C-$NH_2$ | CH | CH | ox. | 144-145 |
| 85 | N | H | CH | C-4-$C_5H_4N$ | CH | CH | ox. | 281-282 |
| 86 | N | H | CH | C-3-$C_4H_3O$ | CH | CH | ox. | 310-311 |
| 87 | N | H | CH | CH | 2-$C_4H_4N$ | CH | HBr | 324-325 |

The compounds of the present invention were studied as regards their affinity with respect to nicotinic receptors containing the $\alpha_4\beta_2$ subunit according to the methods described by Anderson and Arneric, *Eur. J. Pharmacol* (1994) 253 261, and by Hall et al., *Brain Res.* (1993) 600 127.

Male Sprague Dawley rats weighing 150 to 200 g are decapitated and the entire brain is removed quickly, homogenized in 15 volumes of 0.32 M sucrose solution at 4° C. and then centrifuged at 1000×g for 10 min. The pellet is discarded and the supernatant is centrifuged at 20,000×g for 20 min at 4° C. The pellet is recovered and homogenized using a Polytron™ mill in 15 volumes of double-distilled water at 4° C., followed by centrifugation at 8000×g for 20 min. The pellet is discarded and the supernatant and the "buffy coat" are centrifuged at 40,000×g for 20 min, the pellet is recovered, resuspended in 15 ml of double-distilled water and centrifuged again at 40,000×g, before being stored at −80° C.

On the day of the experiment, the tissue is thawed slowly and suspended in 3 volumes of buffer. 150 μl of this membrane suspension are incubated at 4° C. for 120 min in the presence of 100 μl of 1 nM [$^3$H]cytisine in a final volume of 500 μl of buffer, in the presence or absence of test compound.

The reaction is stopped by filtration on Whatman GF/B™ filters pretreated with polyethyleneimine, the filters are rinsed with 2×5 ml of buffer at 4° C. and the radioactivity retained on the filter is measured by liquid scintigraphy. The non-specific binding is determined in the presence of 10 µM (−)-nicotine; the non-specific binding represents 75 to 85% of the total binding recovered on the filter. For each concentration of test compound, the percentage of inhibition of the specific binding of [$^3$H]cytisine is determined, followed by calculating the $IC_{50}$ value, which is the concentration of compound which inhibits the specific binding by 50%.

The $IC_{50}$ values for the purest compounds of the invention are between 1 and 10 µM.

The compounds of the invention were also studied as regards their affinity with respect to nicotinic receptors containing the α7 subunit, according to the methods described by Marks and Collins, *J. Pharmacol. Exp. Ther.* (1982) 22 564 and Marks et al., *Mol. Pharmacol.* (1986) 30 427.

Male OFA rats weighing 150 to 200 g are decapitated, the entire brain is removed quickly and homogenized using a Polytron™ mill in 15 volumes of a 0.32 M sucrose solution at 4° C., followed by centrifugation at 1000×g for 10 min. The pellet is discarded and the supernatant is centrifuged at 8000×g for 20 min at 4° C. The pellet is recovered and homogenized using a Polytron™ mill in 15 volumes of double-distilled water at 4° C., followed by centrifugation at 8000×g for 20 min. The pellet is discarded and the supernatant and the buffy coat are centrifuged at 40,000×g for 20 min. The pellet is recovered, resuspended with 15 volumes of double-distilled water at 4° C. and centrifuged again at 40,000×g for 20 min, before storing it at −80° C.

On the day of the experiment, the tissue is thawed slowly and suspended in 5 volumes of buffer. 150 µl of this membrane suspension is preincubated at 37° C. for 30 min, in the dark, in the presence or absence of the test compound. Next, the membranes are incubated for 60 min at 37° C., in the dark, in the presence of 50 µl of 1 nM [$^3$H]α-bungarotoxin in a final volume of 250 µl of 20 mM HEPES, 0.05% polyethyleneimine buffer. The reaction is stopped by filtration through Whatman GF/C™ filters pretreated for 3 hours with 0.5% polyethyleneimine. The filters are rinsed with 2×5 ml of buffer at 4° C. and the radioactivity retained on each filter is measured by liquid scintigraphy. The non-specific binding in the presence of α-bungarotoxin at 1 µM final is determined; the non-specific binding represents about 60% of the total binding recovered on the filter. For each concentration of test compound, the percentage of inhibition of the specific binding of [$^3$H] α-bungarotoxin is determined, followed by calculation of the $IC_{50}$ value, which is the concentration of compound which inhibits the specific binding by 50%.

The $IC_{50}$ values for the purest compounds of the invention are between 0.005 and 0.15 µM.

The preceding results show that the compounds of the invention are selective ligands for the $α_7$ subunits of the nicotinic receptor.

The results of the various tests suggest the use of the compounds in the treatment or prevention of disorders associated with dysfunction of the nicotinic receptors, especially in the central nervous system.

These disorders comprise cognitive impairment, more specifically memory impairment, but also attention impairment, associated with Alzheimer's disease, pathological ageing (Age Associated Memory Impairment, AAMI), Parkinson's disease, trisomy 21 (Down's syndrome), Korsakoff's alcoholic syndrome and vascular dementia (multi-infarct dementia, MID).

The compounds of the invention may also be useful in the treatment of the motor disorders observed in Parkinson's disease or other neurological diseases such as Huntington's chorea, Tourette's syndrome, tardive dyskinesia and hyperkinesia.

The compounds of the invention can also constitute a curative or symptomatic treatment for acute neurodegenerative pathologies such as strokes and cerebral hypoxic episodes, and also chronic neurodegenerative pathologies, for instance Alzheimer's disease. They may also be used in cases of psychiatric pathologies: schizophrenia, depression, anxiety, panic attacks, compulsive and obsessive behavior.

They can prevent the symptoms caused by withdrawal from tobacco, from alcohol and from various substances that induce a dependency, such as cocaine, LSD, cannabis and benzodiazepines.

It is moreover known that activation of the vascular nicotinic receptors stimulates the proliferation of endothelial cells and arterial smooth muscle, reduces their apoptosis and increases the formation of capillary tubes in vitro. In vivo, these effects are reflected by an angiogenic action, which is well documented in models of ischaemia of the lower limbs. Nicotine administered chronically increases the capillary density, the diameter of the collateral arteries and the blood perfusion into ischaemic skeletal muscle. The angiogenic and arteriogenic effects of nicotine appear concomitantly with the increase in the recruitment of monocytes, and are partially mediated by the release of angiogenic factors such as nitrogen monoxide and VEGF (vascular endothelial growth factor). By its angiogenic activity, nicotine, applied topically, accelerates skin cicatrization in the case of diabetic animals.

Given the activities summarized above, the therapeutic indications are the treatment of ischaemia of the lower limbs, obliterative arteritis of the lower limbs (PAD: peripheral arterial disease), cardiac ischaemia (stable angina), myocardial infarction, cardiac insufficiency, cutaneous cicatrization deficiency in diabetic patients, and varicose ulcers of venous insufficiency.

For each of the abovementioned pathologies, the treatment will be performed with the nicotinic agent alone and/or in combination with the reference medicinal products indicated in the pathology.

Consequently, a subject of the present invention is also pharmaceutical compositions containing an effective dose of at least one compound according to the invention, in base form or in the form of a pharmaceutically acceptable salt or solvate, and as a mixture, where appropriate, with suitable excipients.

The said excipients are chosen according to the pharmaceutical form and the desired mode of administration.

The pharmaceutical compositions according to the invention may thus be intended for oral, sublingual, subcutaneous, intramuscular, intravenous, topical, intratracheal, intranasal, transdermal, rectal or intraocular administration.

The unit forms of administration may be, for example, tablets, gel capsules, granules, powders, oral or injectable solutions or suspensions, transdermal patches or suppositories. Ointments, lotions, and eye drops may be envisaged for topical administration.

The said unit forms are dosed to allow a daily administration of from 0.01 to 20 mg of active principle per kg. of body weight, according to the presentation form.

In order to prepare tablets, a pharmaceutical vehicle which may be composed of diluents such as, for example, lactose, microcrystalline cellulose, starch and formulation adjuvants, for instance binders (polyvinylpyrrolidone, hydroxypropylmethylcellulose, etc.), glidants, for instance silica, lubricants, for instance magnesium stearate, stearic acid, glyceryl tribehenate or sodium stearylfumarate is added to the micronized or non-micronized active principle. Wetting agents or surfactants such as sodium lauryl sulfate may also be added.

The preparation techniques may be direct tableting, dry granulation, wet granulation or hot melting.

The tablets may be plain, coated, for example with sucrose, or coated with various polymers or other suitable materials. They may be designed to allow a rapid, delayed or sustained release of the active principle by means of polymer matrices or specific polymers used in the coating.

In order to prepare gel capsules, the active principal is mixed with dry pharmaceutical vehicles (simple mixing, dry or wet granulation, or hot melting) or liquid or semi-solid pharmaceutical vehicles.

The gel capsules may be hard or soft, and uncoated or film-coated, so as to have rapid, sustained or delayed activity (for example for an enteric form).

A composition in the form of a syrup or elixir for administration in the form of drops may contain the active principle together with a sweetener, preferably a calorie-free sweetener, methylparaben or propylparaben as antiseptic, a flavor enhancer and a colorant.

The water-dispersible powders and granules may contain the active principle mixed with dispersants or wetting agents, or dispersants such as polyvinylpyrrolidone, and also with sweeteners and flavor enhancers.

For rectal administration, use is made of suppositories prepared with binders that melt at the rectal temperature, for example cocoa butter or polyethylene glycols.

For parenteral administration, aqueous suspensions, isotonic saline solutions or injectable sterile solutions containing pharmacologically compatible dispersants and/or wetting agents, for example propylene glycol or butylene glycol, are used.

The active principle may also be formulated in the form of microcapsules, optionally with one or more supports or additives, or with a polymer matrix or with a cyclodextrin (transdermal patches, sustained-release forms).

The topical compositions according to the invention comprise a medium that is compatible with the skin. They may especially be in the form of aqueous, alcoholic or aqueous-alcoholic solutions, gels, water-in-oil or oil-in-water emulsions having the appearance of a cream or a gel, microemulsions or aerosols, or alternatively in the form of vesicular dispersions containing ionic and/or nonionic lipids. These presentation forms are prepared according to the usual methods of the fields under consideration.

Finally, the pharmaceutical compositions according to the invention may contain, along with a compound of general formula (I), other active principles that may be useful in the treatment of the disorders and diseases indicated above.

What is claimed is:

1. A compound of formula (I):

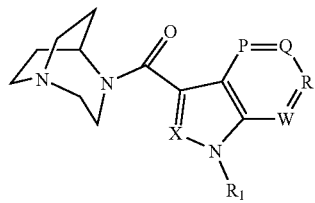

(I)

in which

X represents a nitrogen atom or a group of formula C—$R_2$,

P represents a group of formula C—$R_3$,

Q represents a group of formula C—$R_4$,

R represents a group of formula C—$R_5$,

W represents a group of formula C—$R_6$, or one of the symbols P, Q, R and W represents a nitrogen atom, $R_1$ represents a hydrogen atom or a ($C_1$-$C_6$)alkyl group, $R_2$ represents a hydrogen atom or a ($C_1$-$C_6$)alkyl group, $R_3$, $R_4$, $R_5$ and $R_6$ each represent, independently of each other, a hydrogen or halogen atom, or a ($C_1$-$C_6$)alkyl, ($C_1$-$C_6$)alkoxy, nitro, amino, trifluoromethyl or cyano group, or a group of formula —$NR_7R_8$, —$NR_7C(=O)R_8$, —$NR_7C(=O)NR_8R_9$, —$NR_7C(=O)OR_8$, —$NR_7S(=O)_2NR_8R_9$, —$OR_7$, —$OC(=O)R_7$, —$OC(=O)OR_7$, —$OC(=O)ONR_7R_8$, —$OC(=O)R_7$, —$C(=O)OR_7$, —$C(=O)R_7$, —$C(=O)NR_7R_8$, —$R_7$, —$S(=O)R_7$, —$S(=O)_2R_7$, or —$S(=O)_2NR_7R_8$, $R_7$, $R_8$ and $R_9$ each represent, independently of each other, a hydrogen atom or a linear or branched ($C_1$-$C_6$)alkyl group, a linear or branched ($C_2$-$C_6$)alkenyl group, a linear or branched ($C_2$-$C_6$)alkynyl group, a ($C_3$-$C_8$)-cycloalkyl or ($C_4$-$C_8$)cycloalkenyl group, or a heterocycloalkyl group containing 3 to 8 atoms in the ring, or a ($C_5$-$C_{11}$)bicycloalkyl or ($C_7$-$C_{11}$)bicycloalkenyl group, a heterobicycloalkyl group containing 5 to 11 atoms in the ring, a bicycloheteroalkenyl group containing 5 to 11 atoms in the ring, or a ($C_6$-$C_{11}$)aryl or heteroaryl group containing 5 to 12 atoms in the ring, $R_7$, $R_8$ and $R_9$ may be optionally substituted, independently of each other, with a halogen atom or a ($C_1$-$C_6$)alkyl, ($C_1$-$C_6$)alkoxy, nitro, amino, trifluoromethyl or cyano group, or a group of formula —$NR_{10}R_{11}$, —$NR_{10}C(=O)R_{11}$, —$NR_{10}(=O)NR_{11}R_{12}$, —$NR_{10}(=O)OR_{11}$, —$NR_{10}S(=O)_2NR_{11}R_{12}$, —$OR_{10}$, —$OC(=O)R_{10}$, —$OC(=O)OR_{10}$, —$OC(=O)ONR_{10}R_{11}$, —$OC(=O)R_{10}$, —$C(=O)OR_{10}$, —$C(=O)R_{10}$, —$C(=O)NR_{10}R_{11}$, —$R_{10}$, —$S(=O)R_{10}$, —$S(=O)_2R_{10}$, —$S(=O)_2NR_2R_{11}$, $R_{10}$, $R_{11}$ and $R_{12}$ each represent, independently of each other, a hydrogen atom or a linear or branched ($C_1$-$C_6$) alkyl group, a linear or branched ($C_2$-$C_6$)alkenyl group, a linear or branched ($C_2$-$C_6$)alkynyl group, a ($C_3$-$C_8$)-cycloalkyl or ($C_4$-$C_8$)cycloalkenyl group, a heterocycloalkyl group containing 3 to 8 atoms in the ring, a ($C_5$-$C_{11}$)bicycloalkyl or ($C_7$-$C_{11}$)bicycloalkenyl group, a heterobicycloalkyl group containing 5 to 11 atoms in the ring, a bicycloheteroalkenyl group containing 5 to 11 atoms in the ring, or a ($C_6$-$C_{ii}$)aryl or heteroaryl group containing 5 to 12 atoms in the ring, $R_{10}$, $R_{11}$ and $R_{12}$ may be optionally substituted, independently of each other, with a halogen atom or a ($C_1$-$C_6$) alkyl, ($C_1$-$C_6$)alkoxy, nitro, amino, trifluoro-methyl or cyano group, or —$NR_{13}R_{14}$, —$NR_{13}C(=O)R_{14}$, —$NR_{13}C(=O)NR_{14}R_{15}$, —$NR_{13}C(=O)OR_{14}$, —$NR_{13}S(=O)_2NR_{14}R_{15}$, —$OR_{13}$, —$OC(=O)R_{13}$, —$OC(=O)OR_{13}$, —$OC(=O)ONR_{13}R_{14}$, —$OC(=O)R_{13}$, —$C(=O)OR_{13}$, —$C(=O)R_{13}$, —$C(=O)NR_{13}R_{14}$, —$R_{13}$, —$S(=O)R_{13}$, —$S(=O)_2R_{13}$, —$S(=O)_2NR_{13}R_{14}$, $R_{13}$, $R_{14}$ and $R_{15}$ each represent, independently of each other, a hydrogen atom or a linear or branched (C1—C6)alkyl group, a linear or branched ($C_2$-$C_6$)alkenyl group, a linear or branched ($C_2$-$C_6$)alkynyl group, a ($C_3$-$C_8$)-cycloalkyl or ($C_4$-$C_8$)cycloalkenyl group, a heterocycloalkyl group containing 3 to 8 atoms in the ring, a ($C_5$-$C_{11}$)bicycloalkyl or ($C_7$-$C_{11}$)bicycloalkenyl group, a heterobicycloalkyl group containing 5 to 11 atoms in the ring, a bicycloheteroalkenyl group containing 5 to 11 atoms in the ring or a $(C_6-C_{11})$aryl or heteroaryl group containing 5 to 12 atoms in the ring, and $R_3$ and $R_4$, or $R_4$ and $R_5$, or $R_5$ and $R_6$, may together form, with the two carbon atoms that bear them, another aromatic or heteroaromatic ring containing 6 atoms in the ring, optionally substituted with 1 to 4 substituents chosen from those defined for $R_7$, $R_8$ and $R_9$, in base form or in the form of an addition salt with an acid.

2. The compound according to claim 1, wherein X represents a group of formula C—$R_2$.

3. The compound according to claim 2, wherein P, Q, R and W each represent, respectively, a group of formula C—$R_3$, C—$R_4$, C—$R_5$ and C—$R_6$.

4. The compound according to claim 2, wherein one of the symbols P, Q, R and W represents a nitrogen atom.

5. The compound according to claim 1, wherein X represents a nitrogen atom.

6. The compound according to claim 5, wherein P, Q, R and W each represent, respectively, a group of formula C—$R_3$, C—$R_4$, C—$R_5$ and C—$R_6$.

7. The compound according to claim 5, wherein one of the symbols P, Q, R and W represents a nitrogen atom.

8. A process for preparing a compound according to claim 1, comprising:
reacting 1,4-diazabicyclo[3.2.2]nonane with a compound of formula (III)

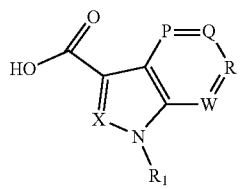

(III)

in which X, P, Q, R, W and $R_1$ are as defined in claim 1, in the presence of a coupling agent and in a solvent, optionally after a prior step of converting the carboxylic acid function into an acid chloride function.

9. A process for preparing a compound according to claim 1, comprising:
reacting 1,4-diazabicyclo[3.2.2]nonane with a compound of formula (IV)

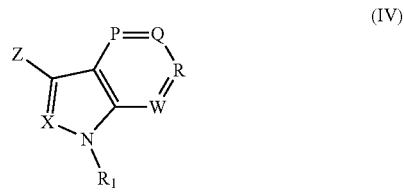

(IV)

in which X, P, Q, R, W and $R_1$ are as defined in claim 1 and Z represents a bromine or iodine atom, in the presence of carbon monoxide, a palladium catalyst and a base, in a solvent.

10. A pharmaceutical composition comprising a compound according to claim 1 and an excipient.

11. A pharmaceutical composition comprising a compound according to claim 2 and an excipient.

12. A pharmaceutical composition comprising a compound according to claim 3 and an excipient.

13. A pharmaceutical composition comprising a compound according to claim 4 and an excipient.

14. A pharmaceutical composition comprising a compound according to claim 5 and an excipient.

15. A pharmaceutical composition comprising a compound according to claim 6 and an excipient.

16. A pharmaceutical composition comprising a compound according to claim 7 and an excipient.

* * * * *